US008512763B2

(12) United States Patent
Kempen

(10) Patent No.: US 8,512,763 B2
(45) Date of Patent: Aug. 20, 2013

(54) **COMBINATIONS OF 4 BROMO 2-(4-CHLOROPHENYL)-5-(TRIFLUOROMETHYL)-1*H*-PYRROLE-3-CARBONITRILE AND METAL COMPOUNDS**

(75) Inventor: Tony Mathilde Jozef Kempen, Kapellen (BE)

(73) Assignee: Janssen Pharmaceutica, NV (BE)

( * ) Notice: Subject to any disclaimer, the term of this patent is extended or adjusted under 35 U.S.C. 154(b) by 21 days.

(21) Appl. No.: 13/486,045

(22) Filed: Jun. 1, 2012

(65) Prior Publication Data

US 2012/0234203 A1 Sep. 20, 2012

Related U.S. Application Data

(62) Division of application No. 12/162,638, filed as application No. PCT/EP2007/050927 on Jan. 31, 2007.

(30) Foreign Application Priority Data

Feb. 1, 2006 (EP) .................................. 06101124

(51) Int. Cl.
*A01N 59/00* (2006.01)
*A01N 59/20* (2006.01)
*A01N 55/00* (2006.01)

(52) U.S. Cl.
USPC ........................... 424/633; 424/632; 514/500

(58) Field of Classification Search
USPC .................. 424/633, 632; 514/500
See application file for complete search history.

(56) References Cited

U.S. PATENT DOCUMENTS

| 5,874,476 A * | 2/1999 | Hsu et al. ..................... 514/640 |
| 6,069,189 A | 5/2000 | Kramer et al. |
| 6,291,549 B1 | 9/2001 | Metchel et al. |
| 7,659,397 B2 | 2/2010 | Hidaka |
| 2006/0089352 A1 | 4/2006 | Bruns et al. |
| 2006/0246097 A1 | 11/2006 | Hidaka |
| 2008/0090938 A1 | 4/2008 | Quaiser et al. |
| 2008/0175812 A1 | 7/2008 | Seabrook et al. |
| 2009/0017135 A1 | 1/2009 | Kempen |
| 2009/0093443 A1 | 4/2009 | Kempen |
| 2010/0178357 A1 | 7/2010 | Kempen |
| 2011/0160258 A1 | 6/2011 | Van der Flaas et al. |
| 2011/0160275 A1 | 6/2011 | Van der Flaas et al. |
| 2011/0237632 A1 | 9/2011 | Kempen |

FOREIGN PATENT DOCUMENTS

| EP | 0312723 B1 | 12/1993 |
| EP | 0746979 A1 | 12/1996 |
| EP | 0831134 A1 | 3/1998 |
| EP | 1769680 B1 | 4/2010 |
| JP | 2001-502732 A | 2/2001 |
| WO | WO 95/05739 A1 | 3/1995 |
| WO | WO 95/06043 A1 | 3/1995 |
| WO | WO 97/42823 A1 | 11/1997 |
| WO | WO 98/12269 A1 | 3/1998 |
| WO | WO 98/17732 A1 | 4/1998 |
| WO | WO 01/95718 A1 | 12/2001 |
| WO | WO 03/039256 A | 5/2003 |
| WO | WO 03039256 A1 * | 5/2003 |
| WO | WO 2005/025313 A1 | 3/2005 |
| WO | WO 2005040122 A1 * | 5/2005 |
| WO | WO 2005/075581 A1 | 8/2005 |
| WO | WO 2006/080890 A1 | 8/2006 |
| WO | WO 2007/088172 A2 | 8/2007 |
| WO | WO 2007/116051 A1 | 10/2007 |
| WO | WO 2012/001027 A2 | 1/2012 |

OTHER PUBLICATIONS

Kull et al., "Mixtures of Quaternary Ammonium Compounds and Long-chain Fatty Acids as Antifungal Agents.", Applied Microbiology, 1961, vol. 9, pp. 538-541.
Limpel et al., "Weed control by dimethyl tetrachloroterephthalate alone and in certain combinations." Proc. Northeast Weed Control Conf., 1962, pp. 48-53, vol. 16.
Colby et al., "Calculating Synergistic and Antagonistic Responses of Herbicide Combinations.", Weeds, Jan. 1967, pp. 20-22, vol. 15(1), Weed Science Society of America.
Richer, D.L., "Synergism—a patent view.", Pestic Sci. 1987, pp. 309-315, vol. 19(4).
Del Amo, B., et al: "A multipurpose compound for protective coatings", Colloids and Surfaces. A, Physicachemical and Engineering Aspects, Elsevier, Amsterdam, NL, vol. 324, No. 1-3, Jul. 1, 2008, pp. 58-64, XP022735387, ISSN: 0927-7757.
Copper Development Association, CDA Technical Note TN11, 1972, pp. 1-22.
Raymond A. Cloyd (2011). Pesticide Mixtures, Pesticides—Formulations, Effects, Fate, Margarita Stoytcheva(Ed.), p. 69-80, InTech, Available from: http://www.intechopen.com/articles/show/title/pesticide-mixtures.
International Preliminary Examination Report and Written Opinion, PCT/EP2007/050927, date of mailing Nov. 1, 2007.
PCT counterpart to U.S. Appl. No. 10/494,751, International Preliminary Examination Report, PCT/EP2002/12376, date of mailing Mar. 12, 2003.

(Continued)

Primary Examiner — Janet Epps-Smith
Assistant Examiner — Courtney Brown

(57) ABSTRACT

The present invention relates to combinations of 4-bromo-2-(4-chloro-phenyl)-5-(trifluoromethyl)-1H-pyrrole-3-carbonitrile, or a salt thereof, and copper or zinc compounds which provide an improved protecting effect against fouling organisms. More particularly, the present invention relates to compositions comprising a combination of 4-bromo-2-(4-chlorophenyl)-5-(trifluoromethyl)-1H-pyrrole-3-carbonitrile, or a salt thereof, together with one or more copper or zinc compounds selected from $Cu_2O$, $Cu(OH)_2$, $CuSO_4$, copper pyrithione, CuSCN, $CuCO_3$, ZnO, $ZnCl_2$, $ZnSO_4$, zineb, and zinc pyrithione; in respective proportions to provide a synergistic effect against fouling organisms and the use of these compositions for protecting materials against fouling organisms. This invention thus relates to the field of protection of materials, such as underwater objects, protection of wood, wood products, biodegradable materials and coatings.

7 Claims, No Drawings

(56) References Cited

OTHER PUBLICATIONS

PCT counterpart to U.S. Appl. No. 12/296,353, International Search Report and Written Opinion, PCT/EP2007/053449, date of mailing Aug. 29, 2007.

PCT counterpart to U.S. Appl. No. 12/376,680, International Search Report and Written Opinion, PCT/EP2007/058132, date of mailing Feb. 6, 2008.

PCT counterpart to U.S. Appl. No. 13/132,821, International Search Report and Written Opinion, PCT/EP2009/066796, date of mailing Jan. 25, 2010.

International Search Report and Written Opinion related to the above patent application, PCT/EP2011/060873, date of mailing Jul. 23, 2012.

* cited by examiner

COMBINATIONS OF 4 BROMO 2-(4-CHLOROPHENYL)-5-(TRIFLUOROMETHYL)-1H-PYRROLE-3-CARBONITRILE AND METAL COMPOUNDS

CROSS REFERENCE TO RELATED APPLICATIONS

This application is a divisional of parent application Ser. No. 12/162,638, filed Jul. 30, 2008, which application is the national stage of Application No. PCT/EP2007/050927, filed Jan. 31, 2007, which application claims priority from European Patent Appl. No. 06101124.3, filed Feb. 1, 2006.

The present invention relates to combinations of 4-bromo-2-(4-chloro-phenyl)-5-(trifluoromethyl)-1H-pyrrole-3-carbonitrile, or a salt thereof, and copper or zinc compounds which provide an improved protecting effect against fouling organisms. More particularly, the present invention relates to compositions comprising a combination of 4-bromo-2-(4-chlorophenyl)-5-(trifluoromethyl)-1H-pyrrole-3-carbonitrile, or a salt thereof, together with one or more copper or zinc compounds selected from $Cu_2O$, $Cu(OH)_2$, $CuSO_4$, copper pyrithione, CuSCN, $CuCO_3$, ZnO, $ZnCl_2$, $ZnSO_4$, zineb, and zinc pyrithione; in respective proportions to provide a synergistic effect against fouling organisms and the use of these compositions for protecting materials against fouling organisms.

It has now been found that the combination of 4-bromo-2-(4-chloro-phenyl)-5-(trifluoromethyl)-1H-pyrrole-3-carbonitrile (hereinafter referred to as component I) and a copper or zinc compound selected from $Cu_2O$, $Cu(OH)_2$, $CuSO_4$, copper pyrithione, CuSCN, $CuCO_3$, ZnO, $ZnCl_2$, $ZnSO_4$, zineb, and zinc pyrithione (hereinafter referred to as a component II), has a synergistic effect on the control of fouling organisms. As used herein, "control" is defined to include the inhibition of attachment or settlement of fouling organisms to the surface of an object, the removal of fouling organisms that are attached to the surface of an object, and the growth of fouling organisms.

4-Bromo-2-(4-chlorophenyl)-5-(trifluoromethyl)-1H-pyrrole-3-carbonitrile is disclosed in EP-0,312,723 for controlling mollusks. Said compound can be represented by the formula:

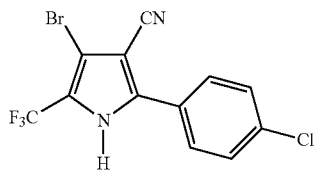

(I)

EP-0,746,979 describes the use of 4-bromo-2-(4-chlorophenyl)-5-(trifluoro-methyl)-1H-pyrrole-3-carbonitrile in antifoulant compositions which are applied to underwater surfaces in order to prevent the attachment of fouling organisms to said underwater surfaces. WO-03/039256 discloses combinations of 4-bromo-2-(4-chloro-phenyl)-5-(trifluoromethyl)-1H-pyrrole-3-carbonitrile with bethoxazin, DCOIT, tolylfluanid and dichlofluanid for protecting materials against fouling organisms.

The copper and zinc compounds, also referred to as components (II), are the following:
component (II-a): $Cu_2O$ or copper (I) oxide;
component (II-b): $Cu(OH)_2$ or copper (II) hydroxide;
component (II-c): $CuSO_4$ or copper (II) sulfate;
component (II-d): copper pyrithione is a complex of one or two pyrithione molecules with copper ligands, in particular $Cu^+$ or $Cu^{2+}$, thereby forming (1-hydroxy-2(1H)-pyridinethionato-O,S) copper (CAS 154592-20-8) or bis(1-hydroxy-2(1H)-pyridinethionato-O,S) copper (CAS 14915-37-8);
component (II-e): CuSCN or copper thiocyanate;
component (II-f): $CuCO_3$ or copper carbonate;
component (II-g): ZnO or zinc (II) oxide;
component (II-h): $ZnCl_2$ or zinc (II) chloride;
component (II-i): $ZnSO_4$ or zinc (II) sulfate;
component (II-j): zineb or zinc ethylenebis(dithiocarbamate); and
component (II-k): zinc pyrithione or (bis(1-hydroxy-2(1H)-pyridinethionato-O,S)-T-4) zinc.

Wherever the term "4-bromo-2-(4-chlorophenyl)-5-(trifluoromethyl)-1H-pyrrole-3-carbonitrile" or component (I) is used throughout this text, it is meant to include said compound both in base or in salt form, the latter being obtained by reaction of the base form with an appropriate acid. Appropriate acids comprise, for example, inorganic acids, such as the hydrohalic acids, i.e. hydrofluoric, hydrochloric, hydrobromic and hydroiodic, sulfuric acid, nitric acid, phosphoric acid, phosphinic acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methyl-benzenesulfonic, cyclohexanesulfamic, 2-hydroxybenzoic, 4-amino-2-hydroxybenzoic and the like acids. Said component (I) may also exist in the form of solvates, such as hydrates.

The copper and zinc compounds as components (II) may also be used in the form of a hydrate. For instance, $CuSO_4$ is available as an anhydrous powder but also exists in hydrated form such as e.g. $CuSO_4.5H_2O$. $ZnSO_4$ is commercially available both as a monohydrate or a heptahydrate. $CuCl_2$ is commercially available as an anhydrous powder and as a dihydrate. Hydrated forms of components (II) are meant to be included in the term "component (II)" as used throughout this text.

Surfaces or objects exposed to humid or aqueous environments are readily colonized by aquatic organisms such as algae, fungi, bacteria, microbes, and aquatic animals such as, e.g. tunicates, hydroids, bivalves, bryozoans, polychaete worms, sponges, barnacles, and mollusks. As these organisms settle on or attach to said surfaces, the value of the exposed objects diminishes. The attachment or settlement of said organisms is also known as 'fouling' of a structure. The exterior, but possibly also the interior of the object may deteriorate, the surface changes, e.g. from smooth, clean and streamlined to rough, foul and turbulent, the weight of the object increases by the deposit of the organisms and their remnants, and the vicinity of the object may become obstructed or encumbered. The function of the object and system involved lowers and the quality of the aqueous environment deteriorates. The common method of controlling the attachment of fouling organisms is by treating the structure to be protected with a coating which comprises an antifouling agent.

The combinations as claimed in the present invention are especially suitable to protect surfaces or objects in constant or frequent contact with water from fouling or attachment or settlement of algae, by applying to said surfaces or objects a composition comprising component (I) and one of the components (II) in respective proportions to provide a synergistic effect against fouling organisms.

Examples of said surfaces or objects are for instance, shiphulls, harbor installations, piers and pilings, drying docks, sluice-gates, locks, mooring masts, buoys, offshore oil rigging equipment, drilling platforms, bridges, pipelines, fishing nets, cables, ballast water tanks, ship reservoirs that draw water from infested bodies of water, recreational equipment, such as surfboards, jet skis, and water skis, and any other object in constant or frequent contact with water.

The invention also provides a method to protect materials, in particular surfaces or objects in frequent or constant contact with water, against fouling organisms by applying to said objects a composition comprising an effective antifouling amount of a combination of component (I) together with one of the components (II) wherein the amount of component (I) and component (II) are in respective proportions to provide a synergistic effect against fouling organisms.

The present invention further provides a method of protecting a surface which comprises applying to the surface a composition comprising an effective antifouling amount of a combination of component (I) together with one of the components (II) wherein the amount of component (I) and component (II) are in respective proportions to provide a synergistic effect against fouling organisms. An especially important use of the method of the invention comprises a method for inhibiting fouling of a ship's hull, which comprises applying to the hull an antifouling composition in accordance with the invention. Fouling on the hulls of ships for example increases frictional drag with a corresponding decrease in speed and maneuverability and an increase in fuel consumption and increased maintenance costs associated with removal of the fouling.

The compositions comprising a combination of component (I) together with one of the components (II) wherein the amount of component (I) and component (II) are in respective proportions to provide a synergistic effect against fouling organisms can be used to protect constructions such as, e.g. swimming pools, baths, cooling water circulation circuits and industrial baths in various installations, e.g. in manufacturing plants or in air-conditioning installations, the function of which can be impaired by the presence and/or the multiplication of fouling organisms. Further examples are buildings and parts of buildings such as floors, outer and inner walls or ceilings, or places suffering from dampness such as cellars, bathrooms, kitchens, washing houses and the like, and which are hot-beds for fouling. Fouling not only is problematic from the viewpoint of hygiene and aesthetics, but also causes economic losses because said buildings and/or decorating materials deteriorate more rapidly than desired.

Another application of the combinations of the present invention is the treatment or disinfection of ballast water to reduce or eliminate the presence of aquatic organisms such as phytoplankton (dinoflagellates and diatoms), crustaceans (crabs, shrimp, copepods, amphipods), rotifers, polychaetes, mollusks, fish, echinoderms, ctenophores, and coelenterates.

The synergistic antifouling compositions of the present invention can also be used in a variety of applications:
  industrial aqueous process fluids, e.g. cooling waters, pulp and paper mill process waters and suspensions, secondary oil recovery systems, spinning fluids, metal working fluids, and the like
  in-tank/in-can protection of aqueous functional fluids, e.g. polymer emulsions, water based paints and adhesives, glues, starch slurries, thickener solutions, gelatin, wax emulsions, inks, polishes, pigment and mineral slurries, rubber latexes, concrete additives, drilling mud's, toiletries, aqueous cosmetic formulations, pharmaceutical formulations, and the like.

The term "fouling organisms" is meant to comprise organisms that attach, settle, grow on or adhere to various kinds of surfaces, in particular in humid or aqueous environments such as, marine waters, fresh waters, brackish waters, rain water, and also cooling water, drainage water, waste water and sewage. Fouling organisms are Algae such as, for example, Microalgae, e.g. *Amphora, Achnanthes, Navicula, Amphiprora, Melosira, Cocconeis, Chlamydomonas, Chlorella, Ulothrix, Anabaena, Phaeodactylum, Porphyridium*; Macroalgae, e.g. *Enteromorpha, Cladophora, Ectocarpus, Acrochaetium, Ceramium, Polysiphonia and Hormidium* sp.; fungi; microbes; tunicates, including members of the class Ascidiacea such as *Ciona intestinalis, Diplosoma listerianium*, and *Botryllus schlosseri*; members of the class Hydrozoa, including *Clava squamata, Hydractinia echinata, Obelia geniculata* and *Tubularia larynx*; bivalves, including *Mytilus edulis, Crassostrea virginica, Ostrea edulis, Ostrea chilensia, Dreissena polymorpha* (zebra mussels) and *Lasaea rubra*; bryozoans, including *Electra pilosa, Bugula neritina*, and *Bowerbankia gracilis*; polychaete worms, including *Hydroides norvegica*; sponges; and members of the class Crustacea, including *Artemia*, and Cirripedia (barnacles), such as *Balanus amphitrite, Lepas anatifera, Balanus balanus, Balanus balanoides, Balanus hameri, Balanus crenatus, Balanus improvisus, Balanus ga/eatus, and Balanus eburneus*; and *Elminius modestus*, and *Verruca*.

The relative proportions of component (I) and one of the components (II) in compositions comprising a combination of component (I) and one of the components (II) are those proportions which result in a synergistic effect against fouling organisms when compared to a composition including, as an active ingredient, either component (I) alone or a component (II) alone. As will be understood by those skilled in the art, the said synergistic effect may be obtained within various proportions of components (I) and (II) in the composition, depending on the kind of fouling organism towards which effect is measured and the substrate to be treated. Based on the teachings of the present application, determination of the synergistic effect of such combinations can be performed according to the procedures of the Poison Plate Assay as described in Experiment 1. As a general rule, however, it may be said that for most fouling organisms the suitable proportions by weight of the amount of component (I) to component (II) in the combinations should lie in the range from 10:1 to 1:10. Particularly, this range is from 8:2 to 2:8, more particularly from 3:1 to 1:3 or 2:1 to 1:2. Another particular ratio of component (I) to component (II) in the compositions of the present invention is a 1:1 ratio between component (I) and one of the components (II).

The quantity of each of the active ingredients in compositions comprising a combination of component (I) and one of the components (II) will be so that a synergistic effect is obtained. In particular it is contemplated that the ready to use compositions of the present invention comprise component (I) in an amount of at least 1 wt % based on the total weight of the composition. More particular such ready to use compositions comprise component (I) in an amount from 1 wt % to 40 wt % based on the total weight of the composition. The amount of component (II) in said ready to use compositions will be so that a synergistic antifouling effect is obtained. In particular the amount of component (II) may range from 1 wt % to 20 wt %, more particular from 2 wt % to 10 wt % based on the total weight of the dry mass of the composition. In many instances the antifouling compositions to be used directly can be obtained from concentrates, such as e.g. emulsifiable concentrates, suspension concentrates, or soluble concentrates, upon dilution with aqueous or organic media, such concentrates being intended to be covered by the term composition as used in the definitions of the present invention. Concentrates used in the form of a paint composition can be diluted to a ready to use mixture in a spray tank shortly before use.

A composition comprising a combination of component (I) and one of the components (II) in respective proportions to provide a synergistic effect against fouling organisms is thus suitably used together with carriers and additives, including wetting agents, dispersing agents, stickers, adhesives, emulsifying agents and the like such as those conventionally employed by the artisan in preparing antifouling compositions. The antifouling compositions of the present invention may further comprise suitable substances known in the art of formulation, such as, for example natural or regenerated mineral substances, solvents, dispersants, surfactants, wetting agents, adhesives, thickeners, binders, anti-freeze agents, repellents, colour additives, corrosion inhibitors, water-repelling agents, siccatives, UV-stabilizers and other active ingredients. Suitable surfactants are non-ionic, cationic and/or anionic surfactants having good emulsifying, dispersing and wetting properties. The term "surfactants" will also be understood as comprising mixtures of surfactants.

Antifouling compositions comprising a combination of component (I) and one of the components (II) in respective proportions to provide a synergistic effect against fouling organisms may be prepared in any known manner, for instance by homogeneously mixing, coating and/or grinding the combination of active ingredients (i.e. component (I) and one of the components (II)), in a one-step or multi-steps procedure, with the selected carrier material and, where appropriate, the other additives such as surface-active agents, dispersants, thickeners, binders, colour additives, corrosion inhibitors and the like.

Suitable carriers for solid formulations, such as dusts, dispersable or flowable powders, are any dispersant that does not adversely affect the active ingredients, for example, clays (for example, kaolin, bentonite, acid clay, and the like), talcs (for example, talc powder, agalmatolite powder, and the like), silicas (for example, diatomaceous earth, silicic acid anhydride, mica powder, and the like), alumina, sulfur powder, activated charcoal, and the like. These solid carriers may be used either singly or in combination of two or more species Appropriate carriers for liquid formulations are any liquid that does not adversely affect the active ingredients, for example, water, alcohols (for example, methyl alcohol, ethyl alcohol, ethylene glycol, propylene glycol, diethylene glycol, glycerin, etc.), ketones (for example, acetone, methyl ethyl ketone, etc.), ethers (for example, dioxane, tetrahydrofuran, cellosolve, diethylene glycol dimethyl ether, etc.), aliphatic hydrocarbons (for example, hexane, kerosene, etc.), aromatic hydrocarbons (for example, benzene, toluene, xylene, solvent naphtha, methyl naphthalene, etc.), halogenated hydrocarbons (for example, chloroform, carbon tetrachloride, etc.), acid amides (for example, dimethyl formadide, etc.), esters (for example, methyl acetate ester, ethyl acetate ester, butyl acetate ester, fatty acid glycerin ester, etc.), and nitriles (for example, acetonitrile, etc.). These solvents may be used either singly or in combination of two or more species.

Emulsifiable concentrates of the antifouling compositions according to the present invention can also be obtained upon dilution of the combination of components (I) and (II) with at least a suitable organic solvent (i.e. a liquid carrier) followed by the addition of at least a solvent-soluble emulsifying agent. Solvents suitable for this type of formulation are usually water-immiscible and belong to the hydrocarbon, chlorinated hydrocarbon, ketone, ester, alcohol and amide classes of solvents, and they can be properly selected by those skilled in the art based on the solubility's of components (I) and (II) respectively. Emulsifiable concentrates usually contain, in addition to the organic solvent(s), from about 10 to 50% by weight of the combination of active ingredients, from about 2 to 20% of emulsifying agent(s) and up to 20% other additives such as stabilisers, corrosion inhibitors and the like. The combination of components (I) and (II) may also be formulated as a suspension concentrate, which is a stable suspension of the active ingredients in a (preferably organic) liquid intended to be diluted with water before use. In order to obtain such a non-sedimenting flowable product, it is usually necessary to incorporate therein up to about 10% by weight of at least a suspending agent selected from known protective colloids and thixotropic agents. Other liquid formulations like aqueous dispersions and emulsions, for example obtained by diluting a wettable powder or a concentrate (such as previously described) with water, and which may be of the water-in-oil or the oil-in-water type, also lie within the scope of the present invention.

The present invention also provides protective antifouling compositions, for instance in the form of paints, coatings or varnishes, comprising the said combination of components (I) and (II) together with one or more additives suitable for their formulation. The total amount of the combination of components (I) and (II) in such protective compositions may range from 2 to 10% (w/v). Suitable additives for use in said protective compositions are quite conventional in the art and include, for instance, at least an organic binder (preferably in aqueous form) such as an acrylic or vinyl-based emulsion or rosin compounds; mineral carriers such as calcium carbonate; surface-active agents such as previously described; viscosity regulators; corrosion inhibitors; pigments such as titanium dioxide; stabilisers such as sodium benzoate, sodium hexametaphosphate and sodium nitrite; mineral or organic colorants and the like. The ways of formulating such additives together with the component (I) and one or more components (II) of the present invention is also well within the knowledge of those skilled in the art. Such protective compositions may be used not only to cure and/or limit the damaging effects of fouling organisms but also in order to prevent deterioration to occur on materials which may be subjected to the harmful environment and effects of fouling organisms.

The antifouling compositions according to the present invention can be applied by a number of conventional methods, such as hydraulic spray, air-blast spray, aerial spray, atomising, dusting, scattering or pouring. The most appropriate method will be chosen by those skilled in the art in accordance with the intended objectives and the prevailing circumstances, namely the kind of fouling organism to be controlled, the type of equipment available and the type of material to be protected.

As previously indicated, the combination of components (I) and (II) is preferably applied in the form of compositions wherein both said ingredients are intimately admixed in order to ensure simultaneous administration to the materials to be protected. Administration or application of both components (I) and (II) can also be a "sequential-combined" administration or application, i.e. component (I) and component (II) are administered or applied alternatively or sequentially in the same place in such a way that they will necessarily become admixed together at the site to be treated. This will be achieved namely if sequential administration or application takes place within a short period of time e.g. within less than 24 hours, preferably less than 12 hours. This alternative method can be carried out for instance by using a suitable single package comprising at least one container filled with a formulation comprising the active component (I) and at least one container filled with a formulation comprising an active component (II). Therefore the present invention also encompasses a product containing:
  (a) a composition comprising 4-bromo-2-(4-chloro-phenyl)-5-(trifluoromethyl)-1H-pyrrole-3-carbonitrile, or a salt thereof, as component (I), and
  (b) a composition comprising a component (II), selected from $Cu_2O$, $Cu(OH)_2$, $CuSO_4$, copper pyrithione, CuSCN, $CuCO_3$, ZnO, $ZnCl_2$, $ZnSO_4$, zineb, and zinc pyrithione, as a combination for simultaneous or sequential use, wherein said (a) and (b) are in respective proportions to provide a synergistic effect against fouling organisms.

EXPERIMENT

Poison Plate Assay

Experiment 1

Poison Plate Assay

Name of the primary compound: 4-bromo-2-(4-chloro-phenyl)-5-(trifluoromethyl)-1H-pyrrole-3-carbonitrile as component (I)
Name of the combination partners:
  $Cu_2O$ as component (II-a);
  $Cu(OH)_2$ as component (II-b);
  $CuSO_4.5H_2O$ as component (II-c);
  copper pyrithione, i.e. bis(1-hydroxy-2(1H) pyridinethionato-O,S) copper, as component (II-d);
  CuSCN as component (II-e);
  $CuCO_3$ as component (II-f);
  ZnO as component (II-g);
  $ZnCl_2$ as component (II-h);
  $ZnSO_4.7H_2O$ as component (II-i);
  zineb as component (II-j);
  zinc pyrithione as component (II-k).
Stock solution: 8000 and 80.000 ppm in DMSO
Test combinations:

| % product A + | % product B |
|---|---|
| 100 + | 0 |
| 80 + | 20 |
| 66 + | 33 |
| 50 + | 50 |
| 33 + | 66 |
| 20 + | 80 |
| 0 + | 100 |

Concentrations of total single active ingredient in the toxicity tests: a series of concentrations increasing with steps of 1/3: 0.03-0.04-0.05-0.06-0.08-0.11-0.15-0.20-0.27-0.35-0.47-0.63-0.84-1.13-1.50-2.00-2.67-3.56-4.75-6.33-8.44-11.25-15.00-20.00-26.70-35.60-47.46-63.28-84.38-112.50-150.00-200.00 ppm.
Concentrations of total active ingredient in the combination tests: a series of concentrations increasing with steps of 1/3: 0.08-0.11-0.15-0.20-0.27-0.35-0.47-0.63-0.84-1.13-1.50-2.00-2.67-3.56-4.75-6.33-8.44-11.25-15.00-20.00 ppm.

For combinations with $CuSO_4$, and $ZnS_4$, a different series with 1/3 steps was used: 0.03-0.05-0.06-0.08-0.11-0.14-0.19-0.25-0.34-0.45-0.60-0.80-1.07-1.42-1.90-2.53-3.38-4.50-6.00-8.00 ppm.
Culture medium: algae: BG 11 liquid mineral medium
  *Artemia saline:* artificial seawater
Experimental set up: 24-well plates
Species of algae:

| (1): *Chlorella vulgaris* | CCAP 211/12 |
| (2): *Anabaena cylindrica* | CCAP 1403/2A |
| (3): *Chlamydomonas sphagnophila* | CCAP 11/36E |

Inoculum: algae: 1990 μl of a 1/10 dilution in BG 11 of a two week old culture
  *Artemia:* 1990 μl artificial seawater with 20-40 *Artemia* larvae (24 hours old)
Culture conditions: 21° C., 65% relative humidity, 1000 lux, 16 hour photoperiod
Evaluation: algae: after 3 weeks of exposure
  *Artemia:* after 24 hours of exposure
Synergism between component (I) and one of the components (II) was determined by a commonly used and accepted method described by Kull F. C. et al. in *Applied Microbiology*, 9, 538-541 (1961) using the Synergy Index, which is calculated as follows for two compounds A and B:

$$\text{Synergy Index } (SI) = \frac{Q_a}{Q_A} + \frac{Q_b}{Q_B}$$

wherein:
  $Q_A$ is the concentration of compound A in ppm, acting alone, which produced an end point (e.g. MIC),
  $Q_a$ is the concentration of compound A in ppm, in the mixture, which produced an end point (e.g. MIC),
  $Q_B$ is the concentration of compound B in ppm, acting alone, which produced an end point (e.g. MIC),
  $Q_b$ is the concentration of compound B in ppm, in the mixture, which produced an end point (e.g. MIC).
MIC is the minimum inhibitory concentration, i.e. the lowest concentration of each test compound or mixture of test compounds sufficient to inhibit visible growth.
When the Synergy Index is greater than 1.0, antagonism is indicated. When the SI is equal to 1.0, additivity is indicated. When the SI is less than 1.0, synergism is demonstrated.
When the Synergy Index is greater than 1.0, antagonism is indicated. When the SI is equal to 1.0, additivity is indicated. When the SI is less than 1.0, synergism is demonstrated.

TABLE 1

MIC-values (minimum inhibitory concentration in ppm) and synergy index of various active ingredients and their combination against *Artemia salina*

| Combination | ratio (I) to (II) | MIC-values in ppm | synergy index |
|---|---|---|---|
| (I) + (II-c) | 100 + 0 | 0.14 | — |
| (I) + (II-c) | 80 + 20 | 0.14 | 0.80 |
| (I) + (II-c) | 66 + 33 | 0.19 | 0.91 |
| (I) + (II-c) | 50 + 50 | 0.25 | 0.89 |
| (I) + (II-c) | 33 + 66 | 0.45 | 1.07 |
| (I) + (II-c) | 20 + 80 | 0.60 | 0.86 |
| (I) + (II-c) | 0 + 100 | 200 | — |
| (I) + (II-j) | 100 + 0 | 0.15 | — |
| (I) + (II-j) | 80 + 20 | 0.06 | 0.32 |

TABLE 1-continued

MIC-values (minimum inhibitory concentration in ppm) and synergy index of various active ingredients and their combination against *Artemia salina*

| Combination | ratio (I) to (II) | MIC-values in ppm | synergy index |
|---|---|---|---|
| (I) + (II-j) | 66 + 33 | 0.27 | 1.20 |
| (I) + (II-j) | 50 + 50 | 0.15 | 0.50 |
| (I) + (II-j) | 33 + 66 | 0.20 | 0.45 |
| (I) + (II-j) | 20 + 80 | 0.63 | 0.87 |
| (I) + (II-j) | 0 + 100 | 20 | — |
| (I) + (II-k) | 100 + 0 | 0.20 | — |
| (I) + (II-k) | 80 + 20 | 0.20 | 0.80 |
| (I) + (II-k) | 66 + 33 | 0.11 | 0.37 |
| (I) + (II-k) | 50 + 50 | 0.15 | 0.38 |
| (I) + (II-k) | 33 + 66 | 0.47 | 0.80 |
| (I) + (II-k) | 20 + 80 | 0.47 | 0.49 |
| (I) + (II-k) | 0 + 100 | 20 | — |

TABLE 2

MIC-values (minimum inhibitory concentration in ppm) and synergy index of various active ingredients and their combination against algae

| Combination | algae species | ratio (I) to (II) | MIC-values in ppm | synergy index |
|---|---|---|---|---|
| (I) + (II-c) | (3) | 100 + 0 | 0.34 | — |
| (I) + (II-c) | (3) | 80 + 20 | 0.34 | 0.84 |
| (I) + (II-c) | (3) | 66 + 33 | 0.34 | 0.73 |
| (I) + (II-c) | (3) | 50 + 50 | 0.45 | 0.78 |
| (I) + (II-c) | (3) | 33 + 66 | 0.60 | 0.80 |
| (I) + (II-c) | (3) | 20 + 80 | 0.60 | 0.61 |
| (I) + (II-c) | (3) | 0 + 100 | 1.90 | — |
| (I) + (II-h) | (1) | 100 + 0 | 26.00 | — |
| (I) + (II-h) | (1) | 80 + 20 | 11.25 | 0.70 |
| (I) + (II-h) | (1) | 66 + 33 | 8.44 | 0.66 |
| (I) + (II-h) | (1) | 50 + 50 | 6.33 | 0.62 |
| (I) + (II-h) | (1) | 33 + 66 | 6.33 | 0.75 |
| (I) + (II-h) | (1) | 20 + 80 | 6.33 | 0.85 |
| (I) + (II-h) | (1) | 0 + 100 | 6.33 | — |
| (I) + (II-i) | (3) | 100 + 0 | 0.19 | — |
| (I) + (II-i) | (3) | 80 + 20 | 0.19 | 0.80 |
| (I) + (II-i) | (3) | 66 + 33 | 0.19 | 0.67 |
| (I) + (II-i) | (3) | 50 + 50 | 0.19 | 0.50 |
| (I) + (II-i) | (3) | 33 + 66 | 0.45 | 0.79 |
| (I) + (II-i) | (3) | 20 + 80 | 0.45 | 0.48 |
| (I) + (II-i) | (3) | 0 + 100 | 267 | — |
| (I) + (II-j) | (1) | 100 + 0 | 26.7 | — |
| (I) + (II-j) | (1) | 80 + 20 | 20.0 | 0.75 |
| (I) + (II-j) | (1) | 66 + 33 | 11.25 | 0.42 |
| (I) + (II-j) | (1) | 50 + 50 | 11.25 | 0.42 |

TABLE 2-continued

MIC-values (minimum inhibitory concentration in ppm) and synergy index of various active ingredients and their combination against algae

| Combination | algae species | ratio (I) to (II) | MIC-values in ppm | synergy index |
|---|---|---|---|---|
| (I) + (II-j) | (1) | 33 + 66 | 4.75 | 0.18 |
| (I) + (II-j) | (1) | 20 + 80 | 15.0 | 0.56 |
| (I) + (II-j) | (1) | 0 + 100 | 26.7 | — |

Species of algae:
(1): *Chlorella vulgaris*
(2): *Anabaena cylindrica*
(3): *Chlamydomonas sphagnophila*

The invention claimed is:

1. A composition comprising a combination of 4-bromo-2-(4-chlorophenyl)-5-(trifluoromethyl)-1H-pyrrole-3-carbonitrile, or a salt thereof, as component (I), and as a component (II) a copper compound that is copper pyrithione; whereby component (I) and the component (II) are in respective proportions to provide a synergistic effect against fouling organisms.

2. A composition according to claim 1 wherein the ratio by weight of component (I) to one of the components (II) is 10:1 to 1:10.

3. A composition according to claim 1 wherein the ratio by weight of component (I) to one of the components (II) is 3:1 to 1:3.

4. A composition as claimed in claim 1 wherein the amount of component (I) ranges from 1 wt % to 40 wt % based on the total weight of the composition.

5. A method of protecting materials against fouling organisms, wherein said method comprises administration or application of an antifouling effective amount of a composition according to claim 1.

6. A method of disinfecting ballast water by adding an antifouling effective amount of a composition according to claim 1.

7. A product containing
(a) a composition comprising 4-bromo-2-(4-chloro-phenyl)-5-(trifluoromethyl)-1H-pyrrole-3-carbonitrile, or a salt thereof, as component (I), and
(b) a composition comprising a component (II) that is copper pyrithione,
as a combination for simultaneous or sequential use, wherein said (a) and (b) are in respective proportions to provide a synergistic effect against fouling organisms.

* * * * *